United States Patent [19]

Besomi et al.

[11] 4,442,402

[45] Apr. 10, 1984

[54] PHOTOLUMINESCENCE METHOD OF TESTING DOUBLE HETEROSTRUCTURE WAFERS

[75] Inventors: Paul R. Besomi, Edison; Joshua Degani, Highland Park; Daniel P. Wilt, Scotch Plains, all of N.J.

[73] Assignee: Bell Telephone Laboratories, Incorporated, Murray Hill, N.J.

[21] Appl. No.: 416,474

[22] Filed: Sep. 10, 1982

[51] Int. Cl.³ .............................................. G01R 31/26
[52] U.S. Cl. ............................. 324/158 D; 324/158 R
[58] Field of Search ........... 324/158 R, 158 D, 158 T, 324/73 R; 357/16, 17; 372/43

[56] References Cited

U.S. PATENT DOCUMENTS

| | | | |
|---|---|---|---|
| 4,051,437 | 9/1977 | Lile et al. | 324/158 R |
| 4,287,473 | 9/1981 | Sawyer | 324/158 R |
| 4,313,125 | 1/1982 | Hartman et al. | 357/17 |
| 4,333,051 | 6/1982 | Goodman | 324/158 D |

OTHER PUBLICATIONS

Johnston, Jr., W. D.; "Macroscopic . . ."; Applied Physics Letters; vol. 24; No. 10; May 15, 1974; pp. 494-496.
Henry et al.; "Nonradiative . . ."; Journal of Applied Physics; vol. 48; No. 9; Sep. 1977; pp. 3962-3970.

*Primary Examiner*—Ernest F. Karlsen
*Attorney, Agent, or Firm*—Michael J. Urbano

[57] ABSTRACT

Under photoluminescence (PL) excitation, the lateral spreading of photo-excited carriers can suppress the photoluminescence signal from double heterostructure (DH) wafers containing a p-n junction. In any DH with a p-n junction in the active layer, PL is suppressed if the power of the excitation source does not exceed a threshold value. This effect can be advantageously used for a nondestructive optical determination of the top cladding layer sheet conductance as well as p-n junction misplacement, important parameters for injection lasers and LEDs.

6 Claims, 5 Drawing Figures

PHOTOLUMINESCENCE METHOD OF TESTING DOUBLE HETEROSTRUCTURE WAFERS

BACKGROUND OF THE INVENTION

This invention relates to the testing of semiconductor wafers and, more particularly, to photoluminescence measurements of double heterostructure (DH) wafers.

In the prior art, the position of a p-n junction in semiconductor material is typically determined either by EBIC (electron beam induced current) techniques or by chemical staining techniques, both of which are destructive methods.

Although photoluminescence (PL) is a powerful tool for nondestructive evaluation of semiconductor material, it has not been used for determining p-n junction misplacement. Rather, it is often used for analytical characterizations such as determining bandgap energy and approximate carrier concentration. Scanning PL is a common technique for revealing defects and nonradiative centers in epitaxial layers. In studying nonradiative centers in double heterostructure (DH) material, W. D. Johnston, Jr., *Appl. Phys. Lett.*, Vol. 24, page 494 (1974), found that defects can induce "large dark spots" (LDS) of diminished PL for distances of the order of 100 μm around the defects. C. H. Henry et al, *J. Appl. Phys.*, Vol. 48, page 3962 (1977), later showed that LDS occur around defects within a DH with a p-n junction. Photoexcited minority carriers diffuse across the junction and drift to the defect where they recombine nonradiatively. Others have studied the excitation dependence of the active layer PL in AlGaAs laser heterostructures. They found a highly nonlinear variation of the PL signal with the excitation intensity at low power density levels, which they have attributed to nonradiative surface recombination at the p-n junction.

SUMMARY OF THE INVENTION

In our PL investigations of DH wafers, we have found that charge-spreading gives rise to an excitation power threshold $P_{th}$ below which a PL signal is not observed. The absence of a PL signal at low excitation power below $P_{th}$ is due to lateral spreading of photoexcited carriers parallel to the p-n junction throughout the wafer. This threshold effect is inherent in p-n heterostructures and is not correlated with defects or nonradiative centers in the material. In contrast, when the p-n junction is outside the active layer, the PL signal is linear with excitation power and no threshold effect is observed.

This effect can be advantageously utilized to improve and extend PL evaluation of DH wafers, especially, material grown for p-n junction lasers and LEDs. In particular, it can be used to determine p-n junction misplacement and total sheet conductance of the cladding layer.

In accordance with one aspect of our invention, therefore, a double heterostructure wafer is tested by the following steps: (a) an excitation beam of optical radiation is made incident on the wafer and is absorbed in the active layer, but not in its cladding layers, thereby to generate PL emission from the active layer; (b) the intensity of the excitation beam is varied in order to vary the intensity of the PL emission; (c) the PL emission is detected; (d) the PL emission versus excitation intensity characteristic is determined; (e) those wafers in which the intensity characteristic exhibits a PL threshold are identified as having p-n junctions in the active layer; and (f) those wafers with no such threshold (i.e., those having a linerar characteristic) are identified as having p-n junctions outside the active layer. For standard DH wafers the p-n junction should be in the active layer so in step (e) the wafers would be accepted, whereas in step (f) they would be rejected (or possibly subject to further processing). Conversely, for isotype DH lasers of the type described by R. L. Hartman et al in U.S. Pat. No. 4,313,125 in step (e) the wafers would be rejected (or possibly subject to further processing), and in step (f) they would be accepted.

In accordance with another aspect of our invention, the top cladding layer of the DH should have a total sheet conductance $\Sigma_t$ within a predetermined range, and after step (e), an alternative step (f') is performed in which $\Sigma_t$ is calculated from the measured $P_{th}$ pursuant the following equation:

$$P_{th} = 16 \frac{\Sigma_t \frac{h\nu}{q} \frac{kT}{q}}{1 - e^{-\alpha d_a}} \quad (1)$$

where $h\nu$ is the photon energy of the excitation beam, $kT$ is the thermal energy, $\alpha$ is the absorption coefficient of the active layer, $d_a$ is the thickness of the active layer, e is the base of the natural logarithm, and g is the charge of an electron. As before, those wafers with $\Sigma_t$ within the predetermined range would be accepted, whereas those outside the range would be rejected (or possibly subject to further processing).

BRIEF DESCRIPTION OF THE DRAWING

Our invention, together with its various features and advantages, can be readily understood from the following more detailed description taken in conjunction with the accompanying drawing, in which.

DETAILED DESCRIPTION

Figure 1:
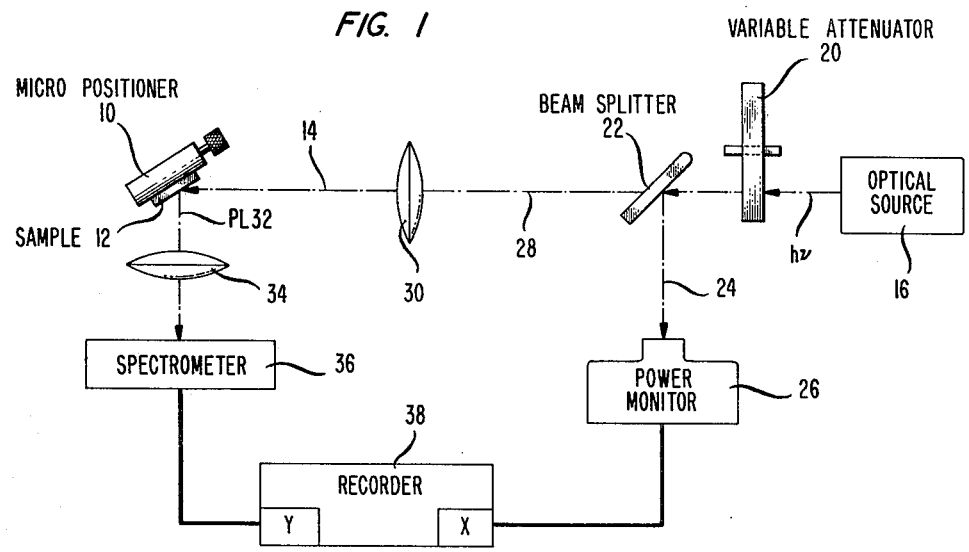
FIG. 1 is a schematic of apparatus useful in practicing our invention.
Figure 5:
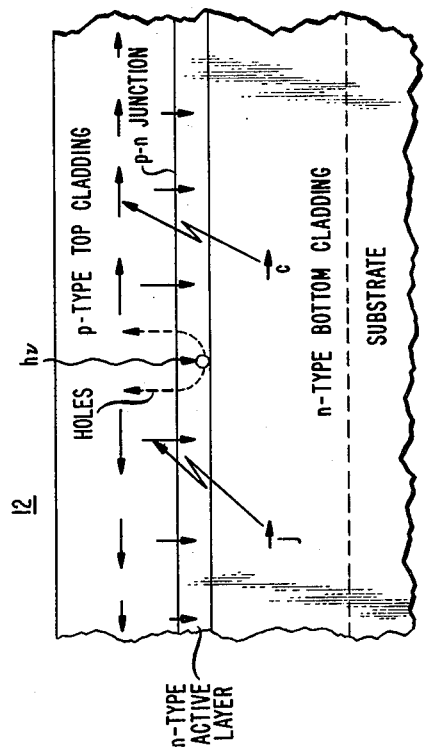
FIG. 5 is schematic of a DH showing the lateral current $\bar{c}$ and the junction current $\bar{j}$ in the lateral photocarrier spreading model.

With reference now to FIG. 1, there is shown schematically apparatus for practicing our invention. The apparatus includes a micropositioner 10 on which a semiconductor sample 12 (i.e., a DH wafer of the type shown in FIG. 5) is mounted. An excitation beam 14 is made incident on the sample 12 and is generated by a suitable optical radiation source 16, preferably a laser, which emits radiation at an energy $h\nu$ absorbed in the active layer, but not in the other layers, as shown in FIG. 5. The intensity (or power) of the laser output beam is varied by attenuator 20 and is then split into two component beams by beam splitter 22; one component beam 24 is directed to a power monitor 26, whereas the other component beam 28 is focused through lens means 30 to produce the excitation beam 14. As a consequence, the excitation beam 14 varies in intensity under control of attenuator 20 and thereby produces PL 32 which also varies in intensity. PL 32 is focussed through lens means 34 onto spectrometer 36, which is set to monitor the PL of the active layer. The electrical outputs of spectrometer 36 and power monitor 26 provide, respectively, the y-input and x-input to recorder 38.

To model the PL response of a DH wafer, we derived a two-dimensional lateral current spreading model. The mechanism of photocarrier spreading in a DH, which has a p-n junction in the active layer and which, therefore, causes the suppression of the PL response at low excitation intensities, is basically similar to that proposed by C. H. Henry et al, supra, to explain the defect-induced LDS effect. However, our treatment is two-dimensional, which, contrary to the Henry et al one-dimensional approach, shows the threshold effect.

Figure 4:
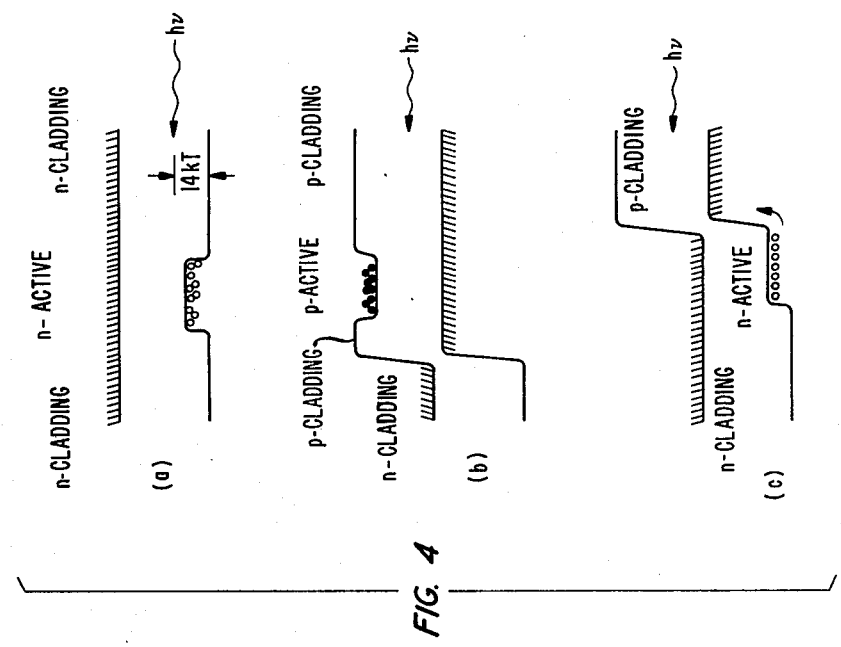
FIG. 4 is a schematic band diagram of various DHs: (a) an n-n-n DH; (b) a misplaced p-n junction in a standard DH; (c) a standard DH with a p-n junction in the active layer.

FIG. 4 shows simplified band structures of various DHs: Part (a), an n-n-n DH with no p-n junction; Part (b), a p-p-p DH with the p-n junction placed outside of the active layer (a misplaced junction), [Part (b) could also depict an isotype DH]; and Part (c) a standard DH with a p-n junction in the active layer.

By way of definition, a p-n junction "in" the active layer includes not only the case where the p-n junction is between the heterojunctions (i.e., the p-n junction is a homojunction), but also the case where the p-n junction is coincident with either heterojunction (i.e., the p-n junction is itself a heterojunction).

In each case shown in FIG. 4, the laser radiation $h\nu$ penetrates through the wide bandgap, top cladding layer and photoexcites the lower bandgap active layer. As can be seen from FIG. 4(a) and FIG. 4(b), the band structure in a DH without a p-n junction in the active layer is such that photoexcited minority carriers in the active layer are bounded by potential barriers, which prevent spreading into the adjacent cladding layers. Thus, the photogenerated minority holes remain essentially localized, except for a negligible lateral diffusion of, for example, 1-2 $\mu$m. The hole recombination rate and the PL signal are thus proportional to the generation rate, or to the excitation power, over a large range of excitation powers.

When there is a p-n junction in the active layer, as shown in FIG. 4(c), photoexcited minority holes can diffuse into the top cladding p-layer and then the holes spread as majority carriers throughout this p-layer. As shown in FIG. 5, these majority carriers induce a current $\bar{c}$ in the p-layer, parallel to the p-n junction. The diffusion of holes from the n-active layer into the p-cladding layer causes a voltage drop which forward biases the p-n junction, resulting in a bias current $\bar{j}$ across the junction. The spatial variation of $\bar{c}$ and $\bar{j}$ determine the hole distribution in the active layer and hence the PL response. It is the solution of the (coupled) equations of $\bar{c}$ and $\bar{j}$ with the appropriate boundary conditions which give rise to equation (1).

The spread of photoexcited carriers in a DH with a p-n junction in the active layer suppresses the PL response below the threshold excitation power given by equation (1). The parameters that set the threshold power have been determined both experimentally and theoretically. This effect can be advantageously used to determine the sheet conductance $\Sigma_t$ of the top cladding layer, a parameter of importance for current spreading in injection lasers.

If for some reason, the active layer and the adjacent portions of the cladding layers, have the same conductivity type, then the only available spreading mechanism for minority carriers is the negligible short range diffusion. Thus, the misplaced junction-type wafer will show a linear PL versus excitation relationship at all power levels—a sensitive test for misplaced junctions in double heterostructure wafers.

In the following example, materials, dimensions and other parameters are provided by way of illustration only and, unless otherwise stated, are not intended to limit the scope of the invention.

EXAMPLE

Steady-state PL measurements were performed on InP-InGaAsP DHs grown by the well-known near-equilibrium LPE technique. The wafers were $\sim 1 \times 1$ cm$^2$ in size and had standard layer structures used in injection lasers. Typically, the wafers comprised an S-doped, (100)-oriented InP substrate (n$\sim 4 \times 10^{18}$ cm$^{-3}$), an n-InP cladding layer (3-4 $\mu$m thick, n$\sim 1 \times 10^{18}$ cm$^{-3}$), an unintentionally doped InGaAsP active layer (E$_g$=0.95 eV, 0.1-0.4 $\mu$m thick, n$\leq 5 \times 10^{16}$ cm$^{-3}$), a p-InP cladding layer (1.5-3.5 $\mu$m thick, p$\sim 2 \times 10^{17}$-$2 \times 10^{18}$ cm$^{-3}$), and a top p$^+$-InGaAsP contact layer (E$_g$=1.2 eV, 0.2-0.8 $\mu$m thick, p$\sim 3$-$5 \times 10^{18}$ cm$^{-3}$). The layer thicknesses were measured using a SEM, and the doping of the layers was determined from the atomic fraction of the dopant in the growth solution, as well as by Hall measurements.

The experimental apparatus is shown in FIG. 1. A CW Nd:YAG laser was used for optical source 16, which had the advantage that only the lower bandgap active layer absorbed light and was photoexcited. the power of the YAG laser could be continuously varied by a variable attenuator 20, and the corresponding PL intensity was plotted on x-y recorder 38. The YAG laser power was monitored using a beam splitter 22 and a calibrated power meter 26 (Pyroelectric Radiometer Rk 5100, manufactured by Laser Precision Corp.). A conventional detection system was used to spectrally resolve the PL signal 32. Spatially resolved measurements were performed by scanning the wafer 12 across the excitation beam 14 using a micropositioner 10. The laser beam was focused to a spot of 25 $\mu$m diameter, unless otherwise stated. The PL was collected by a microscope objective 34 from a region of 100 to 200 $\mu$m around the excitation spot.

Figure 2:
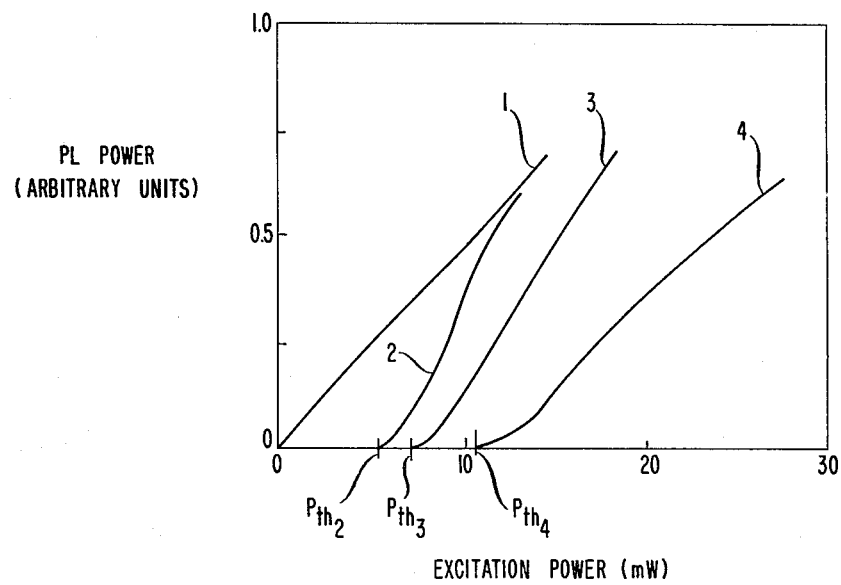
FIG. 2 is a graph of the PL response of various DHs versus the excitation power of a YAG laser; curve 1 shows the response for a DH with no p-n junction; curves 2, 3, and 4, show the response for standard DHs with a p-n junction in the active layer.

The variation of the active layer PL intensity with the YAG laser power was measured in 20 DH wafers. From these measurements the following conclusions were drawn:

(1) The most prominent result for the standard DH material was the onset of a PL signal only above a certain threshold power P$_{th}$ of the YAG laser as given by equation (1). All the DH wafers with a p-n junction in the active layer exhibited such a nonlinear PL response. FIG. 2 shows examples of the variation of the PL power with the YAG laser power for four different wafers. P$_{th}$ varies with layer dopings and thicknesses, but in all cases P$_{th}$ is finite. Curves 2, 3, and 4 correspond to standard DH with a p-n junction in the active layer. The parameters that influence P$_{th}$ in each wafer will be described below.

(2) The PL intensity of a DH with no p-n junction varied linearly with the excitation source power; i.e., $P_{th}=0$ in a manner similar to the PL of a single layer. For example, curve 1 of FIG. 2 corresponds to a DH wafer in which both InP cladding layers were n-doped. Also, standard DH wafers which had a misplaced junction (as revealed by EBIC measurements) had linear PL response of the type shown by curve 1.

As mentioned previously, the PL vanished at low excitation levels (below $P_{th}$) due to lateral spreading of minority photoexcited carriers. The fast, long range spreading resulted from diffusion of photoexcited minority holes across the p-n junction and their subsequent drift as majority holes in the p-layers parallel to the junction and throughout the DH wafer. Since only the carriers recombining within the numerical aperture of the detection system were detected by the optical system, the spreading of carriers suppressed the PL signal. (In principle, if one can monitor the recombination emission from the carriers spread throughout the whole wafer, then—assuming the absence of any nonradiative centers in the wafer—a linear relationship between the PL signal and the excitation source power can be expected. In practice, however, the boundaries of the wafer will induce nonradiative recombination of the spread carriers, so even with the large aperture collecting optics a nonlinear PL will be observed.) At $P > P_{th}$ the photoexcited charge carriers piled up due to the finite sheet resistance of the p-layers and the PL signal appeared. Thus, in the absence of a p-n junction, the usual linear PL characteristic is expected, and, indeed, was observed.

(3) $P_{th}$ was correlated with the sheet conductance of the p-layers of the DH. Wafers with high sheet conductance needed high excitation power for the onset of the PL signal. This result is consistent with the lateral spreading model since, with the high p-layer conductance, spreading of the holes in the p-layer is more efficient.

(4) The threshold YAG laser power depended on the thickness of the active layer. $P_{th}$ was smaller in wafers with thicker active layers. The absorption coefficient of the YAG laser radiation in the quaternary active layer ($E_g = 0.95$ eV) is $1.85 \times 10^4$ cm$^{-1}$. Since the absorption length is longer than the typical active layer thickness used in our measurements, the absorbed laser power in the active layer and the number of photoexcited carriers increased with the active layer thickness. This result indicates that $P_{th}$ is related to the number of photogenerated carriers in the active layer, and not to their density, as is indeed predicted by the lateral spreading model.

(5) PL response was uniform across the wafer (except close to the edges) and no indication of localized recombination centers could be detected. We can therefore assume that localized defects did not have a significant role in the PL response of the wafers studied here.

Figure 3:
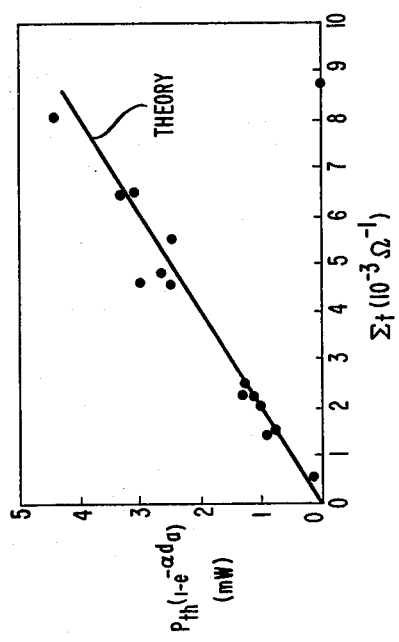
FIG. 3 is a graph of the absorbed power at the onset of PL (i.e., the threshold $P_{th}$) plotted as a function of the total conductance of the p-layers in the standard DH. The single point on the $\Sigma_t$ axis at about $8.8 \times 10^{-3} \Omega^{-1}$ represents a misplaced junction DH. The straight line is derived from theory and follows equation (1)

FIG. 3 summarizes these results. The power absorbed in the active layer at threshold, $P_{th}(1 - e^{-\alpha d_a})$, is plotted as a function of the total sheet conductance of the two p-layers, $$\Sigma_t = \sum_{i=1,2} p_i e \mu_i d_i.$$

Here, $P_{th}$ is the incident YAG laser power (the reflected power was measured and taken into account), $\alpha - 1.85 \times 10^4$ cm$^{-1}$ is the absorption coefficient of the 1.06 μm radiation in the active quanternary layer, $d_a$ is the active layer thickness; $p_i$, $\mu_i$ and $d_i$ ($i=1,2$) are the doping concentration, mobility and the thickness of the two p-layers, respectively. $p_i$ and $\mu_i$ were determined from Hall data or estimated from the melt compositions. The hole mobility in the top InGaAsP contact layer was determined by Hall measurements. The line in FIG. 3 shows the theoretical variation, equation (1). The single point on the conductance axis in FIG. 3 represents a DH with a misplaced junction, which has $P_{th}=0$, as described before.

It is to be understood that the above-described arrangements are merely illustrative of the many possible specific embodiments which can be devised to represent application of the principles of the invention. Numerous and varied other arrangements can be devised in accordance with these principles by those skilled in the art without departing from the spirit and scope of the invention.

In particular, our invention is also applicable to excitation of the active layer through the bottom cladding layer as well as the top cladding layer; e.g., where the bottom cladding layer is formed on a transparent substrate such as InP.

What is claimed is:

1. A manufacturing process including a method of testing a double heterostructure wafer having a narrow bandgap active layer between a pair of wider bandgap cladding layers, the method including the steps of:
   (a) directing an excitation beam of optical radiation at the wafer, the radiation energy being chosen so that it is absorbed in the active layer, but not in the cladding layers, thereby to generate photoluminescence from the active layer,
   (b) varying the intensity of the excitation beam so as to vary the intensity of the photoluminescence,
   (c) detecting the photoluminescence,
   (d) generating a photoluminescence intensity versus excitation beam intensity characteristic,
   (e) selecting the wafer if the characteristic exhibits a photoluminescence threshold $P_{th}$ which indicates that the wafer has a p-n junction in the active layer, and rejecting the wafer if the characteristic exhibits no such threshold which indicates that the wafer has a p-n junction outside the active layer.

2. The method of claim 1 wherein the active layer comprises InGaAsP and the cladding layers comprise InP, and in step (a) the excitation beam is generated by a Nd:YAG laser which emits radiation at a wavelength absorbed in the active layer.

3. The method of claims 1 or 2 wherein the wafer should have a total sheet conductance $\Sigma_t$ within a predetermined range, and after step (e) performing on the selected wafers the additional step of calculating $\Sigma_t$ from $P_{th}$ and rejecting those wafers in which the calculated $\Sigma_t$ falls outside the predetermined range.

4. The method of claim 3 wherein $\Sigma_t$ is calculated from $P_{th}$ using the equation:

$$P_{th} = 16 \frac{\Sigma_t \frac{h\nu}{q} \frac{kT}{q}}{1 - e^{-\alpha d_a}}$$

where $h\nu$ is the photon energy of the radiation, $kT$ is the thermal energy, g is the electron charge, $\alpha$ is the absorption coefficient of the active layer to radiation at $h\nu$, $d_a$ of the active layer, and e is the base of the natural logarithm.

5. A manufacturing process including a method of testing a double heterostructure wafer having a narrow bandgap active layer between a pair of wider bandgap cladding layers, the method including the steps of:
   (a) directing an excitation beam of optical radiation at the wafer, the radiation energy being chosen so that it is absorbed in the active layer, but not in the cladding layers, thereby to generate photoluminescence from the active layer,
   (b) varying the intensity of the excitation beam so as to vary the intensity of the photoluminescence,
   (c) detecting the photoluminescence,
   (d) generating a photoluminescence intensity versus excitation beam intensity characteristic, exhibits a photoluminescence threshold $P_{th}$ which indicates that the wafer has a p-n junction in the active layer, and selecting the wafer if the characteristic exhibits no such threshold which indicates that the wafer has a p-n junction outside the active layer.

6. A manufacturing process including a method of testing a plurality of double heterostructure wafers each having a narrow bandgap active layer between a pair of wider bandgap cladding layers, the method including the steps of:
   (a) directing an excitation beam of optical radiation at a wafer, the radiation energy being chosen so that it is absorbed in the active layer, but not in the cladding layers, thereby to generate photoluminescence from the active layer,
   (b) varying the intensity of the excitation beam so as to vary the intensity of the photoluminescence,
   (c) detecting the photoluminescence,
   (d) generating a photoluminescence intensity versus excitation beam intensity characteristic,
   (e) distinguishing between one wafer if the characteristic exhibits a photoluminescence threshold $P_{th}$ which indicates that the one wafer has a p-n junction in the active layer, and another wafer if the characteristic exhibits no such threshold which indicates that the other wafer has a p-n junction outside the active layer.

* * * * *

UNITED STATES PATENT AND TRADEMARK OFFICE
CERTIFICATE OF CORRECTION

PATENT NO. : 4,442,402
DATED : April 10, 1984
INVENTOR(S) : Paul R. Besomi, Joshua Degani, and Daniel P. Wilt It is certified that error appears in the above-identified patent and that said Letters Patent is hereby corrected as shown below:

Column 4, line 28, "$\leqq$" should read --$\leq$--; line 38, "the" should read --The--. Column 5, line 63, "$p_i e^{uidi}$" should read -- $p_i eu_i d_i$ --. In claim 5, column 7, line 14, after "characteristic," insert --(e) rejecting the wafer if the characteristic--.

Signed and Sealed this

Second Day of April 1985

[SEAL]

Attest:

DONALD J. QUIGG

Attesting Officer     Acting Commissioner of Patents and Trademarks